US011826270B2

United States Patent
McDonagh et al.

(10) Patent No.: US 11,826,270 B2
(45) Date of Patent: Nov. 28, 2023

(54) CONNECTOR FOR TRANSFER OF AN IMPLANT TO A CATHETER

(71) Applicant: Clearstream Technologies Limited, Enniscorthy (IE)

(72) Inventors: Dónal McDonagh, Dublin (IE); Ciaran Giles, Kildare (IE); John O'Shea, Adamstown (IE)

(73) Assignee: Clearstream Technologies Limited, Enniscorthy (IE)

( * ) Notice: Subject to any disclaimer, the term of this patent is extended or adjusted under 35 U.S.C. 154(b) by 0 days.

(21) Appl. No.: 17/777,784

(22) PCT Filed: Oct. 29, 2020

(86) PCT No.: PCT/EP2020/080398
§ 371 (c)(1),
(2) Date: May 18, 2022

(87) PCT Pub. No.: WO2022/089745
PCT Pub. Date: May 5, 2022

(65) Prior Publication Data
US 2022/0346986 A1 Nov. 3, 2022

(51) Int. Cl.
*A61F 2/82* (2013.01)
(52) U.S. Cl.
CPC ........ *A61F 2/82* (2013.01); *A61F 2250/0073* (2013.01)
(58) Field of Classification Search
CPC .......................... A61F 2/82; A61F 2250/0073
See application file for complete search history.

(56) References Cited

U.S. PATENT DOCUMENTS

| 6,143,014 A | 11/2000 | Dehdashtian et al. |
| 6,773,446 B1 | 8/2004 | Dwyer et al. |
| 2019/0125566 A1 | 5/2019 | Walsh |

FOREIGN PATENT DOCUMENTS

| CN | 110251273 A | 9/2019 |
| EP | 903110 A1 | 3/1999 |

(Continued)

OTHER PUBLICATIONS

International Preliminary Report on Patentability dated Jan. 12, 2022, in International Application No. PCT/EP2020/080398.

(Continued)

*Primary Examiner* — Matthew W Schall
(74) *Attorney, Agent, or Firm* — Dinsmore & Shohl LLP

(57) ABSTRACT

A connector for transfer of an implantable device from a loading tube to a delivery catheter, comprising: a first connecting portion (110) having a first distal end (120) configured to receive a delivery catheter (190); a second connecting portion (130) having a second proximal end (150) configured to receive a loading tube (180) extending towards the first distal end, the second connecting portion movably connected to the first connecting portion; and a biasing element (160) connecting the first and second connecting portions, having a relaxed configuration in which the first distal end and the second proximal end are spaced apart by a predetermined distance, and configured to bias the first distal end and second proximal end to the relaxed configuration when the first distal end and second proximal end are moved apart; such that when the loading tube is received, upon receiving the delivery catheter by the first connecting portion, the loading tube is biased to the delivery catheter to form a connection for the transfer of the implantable device.

16 Claims, 6 Drawing Sheets

(56) References Cited

FOREIGN PATENT DOCUMENTS

| JP | 2013540482 | A  | 11/2013 |
|----|------------|----|---------|
| WO | 2012036742 | A2 | 3/2012  |
| WO | 2016172408 | A1 | 10/2016 |

OTHER PUBLICATIONS

Japanese Office Action dated May 30, 2023 pertaining to Japanese application No. 2022-545099 filed Jul. 25, 2022, pp. 1-8.

CONNECTOR FOR TRANSFER OF AN IMPLANT TO A CATHETER

CROSS-REFERENCE TO RELATED APPLICATIONS

This application is a National Stage Entry, under 35 U.S.C. § 371, of International Patent Application No. PCT/EP2020/080398, filed Oct. 29, 2020, the entirety of which is hereby incorporated by reference.

TECHNICAL FIELD

The present disclosure relates to a connector for transfer of an implantable device from a loading tube to a delivery catheter. The disclosure also relates to a method of manufacturing a connector.

BACKGROUND

Medical implants may be designed to be deployed at a particular location in the vasculature. In order to deploy the medical implant, a delivery catheter is directed through the vasculature to a target location, and the medical implant is pushed through the delivery catheter and deployed from the delivery catheter at the target location.

A medical implant may need to be transferred from a loading tube to a delivery catheter. In order to transfer the medical implant from the loading tube to a delivery catheter, the loading tube may be manually inserted into and held inside the delivery catheter during the transfer. Alternatively, a connector connecting the loading tube to the delivery catheter is used. Both methods require the use of both hands, and it is further difficult to ensure whether a proper connection between the loading tube and the delivery catheter is achieved. As the medical implant is often delicate, it is important for the connection between the loading tube and the delivery catheter to be proper. For example, if the loading tube is secured too far away from the delivery catheter entrance, the connection may not provide a smooth transition and this may damage the implant. On the other hand, the loading tube may be damaged if pushed too far into the delivery catheter (for example it may collapse from the inward force of the walls of the catheter).

There is therefore a need for a connector which ensures the connection between the loading tube and the delivery catheter to safely transfer the medical implant.

SUMMARY

According to a first aspect, there is provided a connector for transfer of an implantable device from a loading tube to a delivery catheter, comprising: a first connecting portion having a first distal end configured to receive a delivery catheter; a second connecting portion having a second proximal end configured to receive a loading tube extending towards the first distal end, the second connecting portion movably connected to the first connecting portion; and a biasing element connecting the first and second connecting portions, having a relaxed configuration in which the first distal end and the second proximal end are spaced apart by a predetermined distance, and configured to bias the first distal end and second proximal end to the relaxed configuration when the first distal end and second proximal end are moved apart; such that when the loading tube is received, upon receiving the delivery catheter by the first connecting portion, the loading tube is biased to the delivery catheter to form a connection for the transfer of the implantable device. As a force exerted on the first connecting portion is transmitted to the second connecting portion via the biasing element, the force exerted on the loading tube is dependent on the properties of the biasing element rather than the force exerted by a user, which may prevent the loading tube being forced too far into the delivery catheter.

The connector may further comprise a separating element, wherein when the delivery catheter is received, the separating element is located radially between a proximal end of the delivery catheter and the biasing element. The separating element prevents contact between the implantable device and the biasing element which may prevent damage to the implantable device.

The biasing element may be housed by at least one of the first connecting portion and the second connecting portion, preventing damage to the biasing element.

The biasing element may comprise a resiliently extensible element having a proximal portion connected to the second connecting portion and a distal portion connected to the first connecting portion. The resiliently extensible element is a tensile spring. The biasing element may comprise a resiliently compressible element having a proximal portion connected to the second connecting portion and a distal portion connected to the first connecting portion and the resiliently compressible element may be a compression spring.

The biasing element may be a spring having any suitable spring constant. The spring constant may be selected to that the loading tube is not forced too far into the deliver catheter by the spring. A suitable spring constant will depend on various factors such as the material used for the loading tube and its dimensions and can be determined from routine experimentation.

The first distal end may comprise a male or female screw thread to receive a female or male screw thread, respectively, of a delivery catheter.

The connector may further comprise a stopping element configured to prevent the first distal end and the second proximal end from moving closer than a closest distance to one another.

The first connecting portion may comprise a first tubular body and the second connecting portion may comprise a second tubular body slidable within the first tubular body. The first tubular body may comprise an outer grip. The first connecting portion is more easily handled by a user when the second tubular body is slidable within the first tubular body as the first tubular body has a greater radial extent.

The second connecting portion may comprise a second tubular body and a cap on a distal end of the second tubular body, and the first connecting portion comprises a first tubular body and an inner tubular body within the first tubular body, the inner tubular body extending into the second connecting portion through the cap, the inner tubular body comprising a stopping portion inside the second tubular body, such that separation of the first connecting portion and the second connecting portion is prevented by abutment of the cap and the stopping portion. The first connecting portion may comprise a first tubular body and a cap on a proximal end of the first tubular body, the first connecting portion extending into the second connecting portion through the cap, the second tubular body comprising a stopping portion inside the first tubular body, such that separation of the first connecting portion and the second connecting portion is prevented by abutment of the cap and the stopping portion.

The biasing element may comprise a resiliently compressible element extending between the stopping portion and the cap, and the resiliently compressible element may be a compression spring. The resiliently compressible element may be completely housed by the tubular bodies, the stopping portion and the cap, preventing damage to the element.

The loading tube may be received by the second connecting portion, and the loading tube may be fixedly attached to the second connecting portion, for example by adhesive.

According to a second aspect, there is provided a method of providing a connector for transfer of an implantable device from a loading tube to a delivery catheter, comprising: providing a first connecting portion having a first distal end configured to receive a delivery catheter; providing a second connecting portion having a second proximal end configured to receive a loading tube extending towards the first distal end, the second connecting portion movably connected to the first connecting portion; and providing a biasing element connecting the first and second connecting portions, having a relaxed configuration in which the first distal end and the second proximal end are spaced apart by a predetermined distance, and configured to bias the first distal end and second proximal end to the relaxed configuration when the first distal end and second proximal end are moved apart; such that when the loading tube is received, upon receiving the delivery catheter by the first connecting portion, the loading tube is biased to the delivery catheter to form a connection for the transfer of the implantable device.

The method may further comprise receiving the loading tube by the second connecting portion. When the loading tube is readily provided during manufacture, the assembly process is simpler for a user (who need only attach the connector to the delivery catheter).

The first connecting portion may comprise a first tubular body and an inner tubular body, the inner tubular body comprising a stopping portion, and the seconding connecting portion may comprise a second tubular body and a cap, the first tubular body sized to receive the second tubular body and the second tubular body sized to receive the inner tubular body, the method comprising: providing the biasing element; inserting the inner tubular body into a second distal end of the second tubular body; attaching the cap to a distal end of the second tubular body such that the inner tubular body extends through the cap and the stopping portion is housed by the second tubular body, and such that separation of the first connecting portion and the second connecting portion is prevented by abutment of the cap and the stopping portion; and attaching the inner tubular body to the first tubular body, wherein the second tubular body is slidable within the first tubular body.

The biasing element may comprise a resiliently compressible element and be provided by connecting a proximal portion of the resiliently compressible element to the inner tubular body and a distal portion to the second tubular body, and the resiliently compressible element may be a compression spring.

The biasing element may comprise a resiliently extensible element and be provided by connecting a proximal portion of the resiliently extensible element to the second tubular body and a distal portion to the inner tubular body, and the resilient extensible element may be a tensile spring. The biasing element may comprise a resiliently extensible element and be provided by connecting a proximal portion of the resiliently extensible element to the second tubular body and a distal portion to the second tubular body, and the resiliently extensible element may be a tensile spring.

The first connecting portion may comprise a first tubular body and a cap, the second connecting portion may comprise a second tubular body comprising a stopping portion, the first tubular body sized to receive the second tubular body, and the method may comprise: providing the biasing element; inserting the second tubular body into a proximal end of the first tubular body; and attaching the cap to a proximal end of the first tubular body, such that the second tubular body extends through the cap and the stopping portion is housed by the first tubular body, and such that separation of the first connecting portion and the second connecting portion is prevented by abutment of the cap and the stopping portion.

The biasing element may be a resiliently compressible element and be provided by connecting a proximal portion of the resiliently compressible element to the first tubular body and a distal portion to the second tubular body, and the resiliently compressible element may be a compression spring.

The biasing element may be a resiliently extensible element and be provided by connecting a proximal portion of the resiliently extensible element to the second tubular body and connecting a distal portion to the first tubular body, and the resiliently extensible element may be a tensile spring.

The resiliently compressible element may be provided to extend between the stopping portion and the cap.

According to a third aspect, there is provided a kit of parts comprising a connector according to the first aspect including a loading tube, optionally wherein the loading tube comprises a marker and the loading tube is configured to be received by the second proximal end by inserting the loading tube into the second proximal end until the marker is positioned at the second proximal end. The marker may assist the user in ensuring that the leading tube is correctly received.

BRIEF DESCRIPTION OF THE DRAWINGS

To enable a better understanding of the present disclosure, and to show how the same may be carried into effect, reference will now be made, by way of example only, to the accompanying schematic drawings, in which.

DETAILED DESCRIPTION

Throughout this disclosure, the term "implantable device" or "medical implant" may refer to a device which may be permanently or semi-permanently implanted in a human or animal body.

Figure 1A:
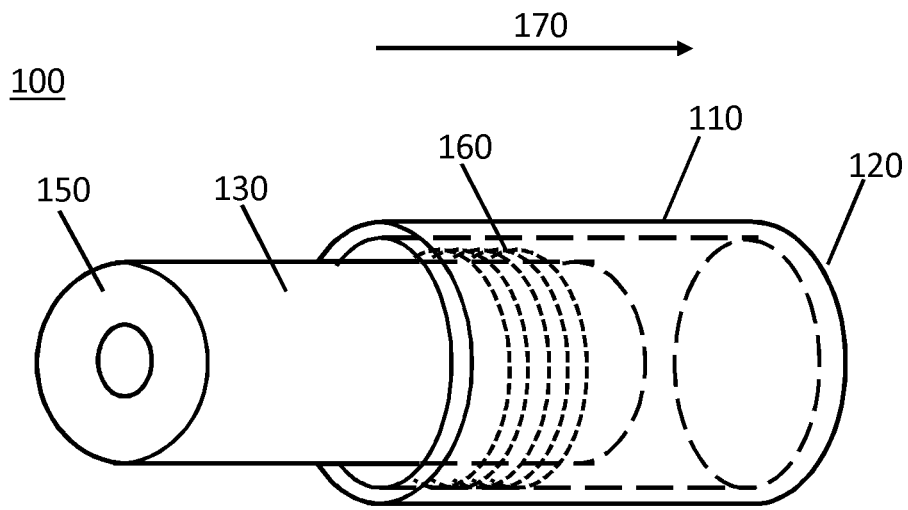
FIG. 1A shows a connector according to one or more embodiments.

FIG. 1A shows a connector 100 for transferring an implantable device (i.e. a medical implant) from a loading tube to a delivery catheter. The connector 100 comprises a first connecting portion 110 having a distal end 120 and a second connecting portion 130 having a proximal end 150. The first and second connecting portions are movable relative to one another. More specifically, the connector 100 comprises a biasing element 160 connecting the first and second connecting portions 110, 130, such that when the first connecting portion 110 is moved in a distal direction (e.g. when a distal force is exerted on the first connecting portion, illustrated by arrow 170), the biasing element 160 biases the second connecting portion 130 in the distal direction. The biasing element 160 has a relaxed configuration in which the distal end 120 and the proximal end 150 are spaced apart by a predetermined distance, and the biasing element 160 is configured to bias the distal end 120 and the proximal end 150 to the relaxed configuration when the distal end 130 and the proximal end 150 are moved apart from the relaxed configuration. Namely, the biasing element 160 is resiliently deformable, and the movement of the first connecting portion 110 in the distal direction deforms the biasing element 160, which results in a biasing force being exerted by the biasing element 160 on the second connecting portion 130 due to deformation of the biasing element.

In the example illustrated by FIG. 1A, the biasing element 160 is a compression spring (i.e. a spring that is configured to transmit the distal biasing force when it is compressed from a relaxed configuration), with a proximal portion connected to first connecting portion 110 and a distal portion connected to the second connecting portion 130. However, any resiliently deformable element capable of transmitting a distal force on the first connecting portion to the second connecting portion may be suitable. For example, in other examples a tensile spring (i.e. a spring that is configured to transmit the distal biasing force when it is extended from a relaxed configuration) is used having a proximal portion connected to the second connecting portion 130 and a distal portion connected to the first connecting portion 110. Other types of spring or biasing element may also be used in in place of the illustrated compression spring.

Furthermore, the position of the biasing element 160 in the connector 100 may also be varied. For example, when a biasing element is used that transmits the distal force by extension from a relaxed configuration, a distal portion of the biasing element 160 may be connected to the first connecting portion 110 at any point along its longitudinal length and a proximal portion of the biasing element may be connected to the second connecting portion 130 at any point along its longitudinal length. Conversely, when a biasing element is used that transmits the distal force by compression from a relaxed configuration, a distal portion of the biasing element 160 may be connected to the second connecting portion 130 at any point along its longitudinal length and a proximal portion of the biasing element 160 may be connected to the first connecting portion 110 at any point along its longitudinal length. In the illustrated example the biasing element 160 is housed by the first connecting portion 110. In some examples, the biasing element 160 may be housed by the second connection portion 130 or located partially or wholly external to the first connecting portion 110.

Figure 1B:
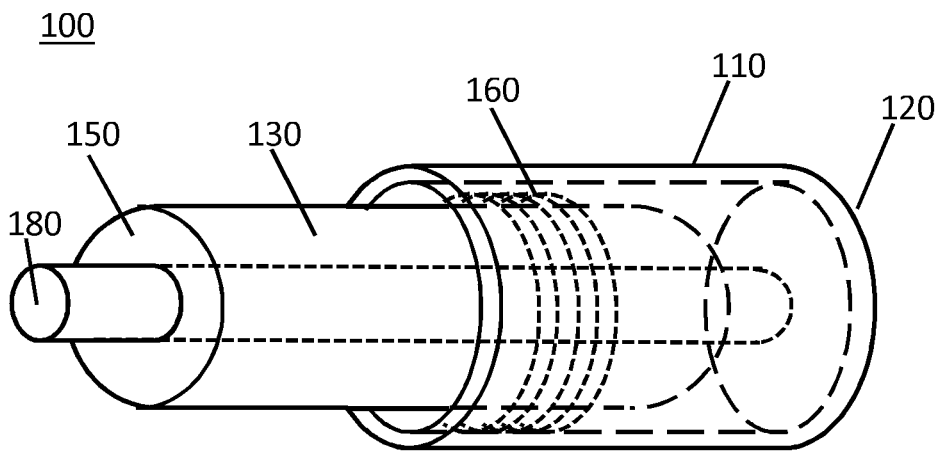
FIG. 1B shows the connector of FIG. 1A with a loading tube received.

The second connecting portion 130 is configured to receive a loading tube 180 at the proximal end 150 such that the loading tube extends toward (i.e. in the direction of) the distal end 120 of the first connecting portion 110, as illustrated in FIG. 1B. For example, the proximal end 150 may comprise an aperture through which the loading tube is configured to extend. The loading tube 180, when received by the second connecting portion 130, may be connected to the second connecting portion 130 by a frictional fit or may be otherwise fixed to the second connecting portion 130, for example via adhesive.

Figure 1C:
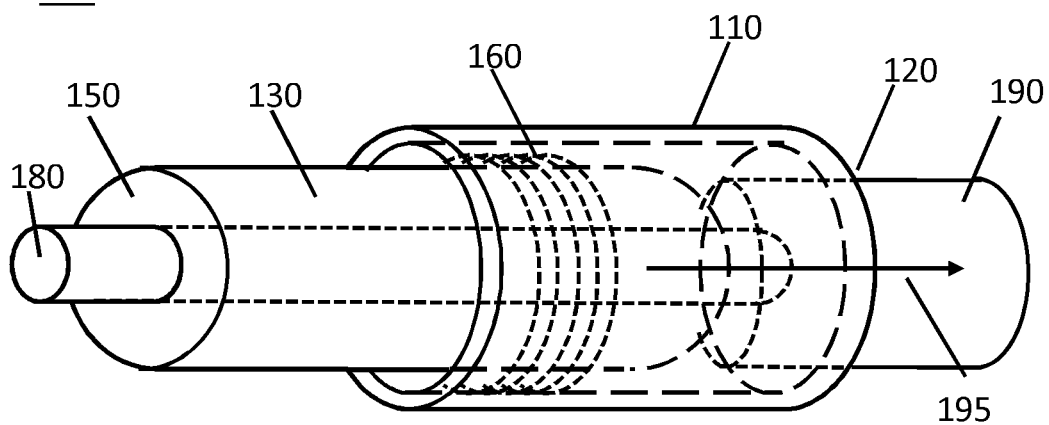
FIG. 1C shows the connector of FIG. 1A with a loading tube and a delivery catheter received.

The first connecting portion 110 is configured to receive a delivery catheter 190 at its distal end 120, as illustrated in FIG. 1C. More specifically, the first connecting portion 110 is configured to hold the delivery catheter 190 in a predetermined position. For example, the distal end 120 may be configured to receive the delivery catheter in a frictional fit, a click fit, a screw fit or any other suitable connecting mechanism to securely hold the delivery catheter 190 in position.

When the loading tube 180 is received as shown in FIG. 1B, a user of the connector 100 connects the delivery catheter 190 to the distal end 120 of the first connecting portion 110 (e.g. by manual manipulation of the first connecting portion 110 and the delivery catheter 190). As a result, a distal force is exerted on the first connecting portion 110 by the user, which is transmitted to the second connecting portion 130 via the biasing element 160, and in turn to the loading tube 180. As the loading tube 180 begins to extend into the delivery catheter 190, a frictional force in the proximal direction is exerted on the loading tube 180 by the delivery catheter 190. This frictional force causes the biasing element 160 to deform away from its relaxed configuration. Advantageously, the deformation of the biasing element 160 acts as a dampener such that the loading tube 180 is not forced to extend too far inside the delivery catheter 190, which could cause damage to the loading tube 180 (for example the loading tube 180 may radially collapse, affecting delivery of the medical implant to the delivery catheter). In other words, the force exerted on the loading tube when connecting the delivery catheter is determined by the properties of the biasing element 160 (e.g. the spring constant) rather than the force exerted by the user of the connector. As such the connector 100 reduces the risk of a user forcing the loading tube 180 too far into the delivery catheter 190 and a proper connection (i.e. having a smooth or continuous transition) is formed by the connector 100.

The configured positions of the loading tube 180 and the delivery catheter 190 may depend on the dimensions of the connecting portions and the requirements of the particular nature of transfer of the medical implant between the loading tube 180 and catheter 190. For example, the connector may be configured to receive the loading tube and delivery catheter such that when both are received in the correct configurations, the loading tube 180 terminates at or partially within the delivery catheter 190. The force exerted by the biasing element 160 on the second connecting portion 130 (and thus the loading tube 180) will depend on the dimensions (e.g. longitudinal lengths) of the connecting portions, the configurations of the loading tube 180 and delivery catheter 190 when received by the connecting portions and the elastic properties of the biasing element 160 (e.g. the spring constant). Therefore, for a given connector 100, a biasing element 160 with a lower spring constant will exert a lower force on the loading tube 180. As such the biasing element 160 can be selected such that the force exerted on the loading tube 180 does not exceed a threshold value. This prevents the loading tube 180 from being damaged whilst also ensuring a proper connection between the loading tube 180 and delivery catheter 190. In some examples, the loading tube 180 may have any suitable outer diameter which is configured to fit inside the corresponding catheter 190 (i.e. an outer diameter which is smaller than the inner diameter of the corresponding catheter 190). For example, the loading tube may have an outer diameter of 11 mm or less, for example between 0.66 mm (2 French gauge) and 3.33 mm (10 French gauge). In a specific example, the loading tube 180 has an inner diameter of 0.027 in (0.6858 mm) and an outer diameter of 0.031 in (0.7874 mm) and the catheter 190 has an inner diameter of 0.038 in (0.9652).

In other examples, there may be provided a proximal portion at the proximal end of the delivery catheter 190 which is sized to fit the loading tube 180 (i.e. the proximal portion has an inner diameter which is greater than the outer diameter of the loading tube). The proximal portion may taper in a distal direction towards the main body of the delivery catheter 190 such that the inner diameter of the delivery catheter (distal to the tapered proximal portion) is less than the inner diameter of the loading tube 180. The proximal portion may be configured to connect to any of the connectors disclosed herein. FIG. 9C shows one such example of a delivery catheter having a tapered proximal portion 950. The tapered portion allows the implant to be smoothly transferred from a loading tube having a larger inner diameter than the inner diameter of the delivery catheter (i.e. the inner diameter of the distal portion of the delivery catheter). Accordingly, the inner diameter of the loading tube may be larger or smaller than the inner diameter of the delivery catheter. In an example, the loading tube 180 has an inner diameter of 0.048 in (1.2192 mm) and an outer diameter of 0.083 in (2.1082 mm) and the catheter 190 has an inner diameter of 0.038 in (0.9652 mm). In yet another example, the loading tube 180 has an inner diameter of 0.065 in (1.651 mm) and an outer diameter of 0.1140 in (2.8956 mm) and the catheter 190 has an inner diameter of 0.056 in (1.4224 mm).

In the illustrated example, the second connecting portion 130 comprises a tubular body slidably received by a tubular body of the first connection portion 110. In some embodiments, the radial extent of the first connecting portion 110 may be less than the radial extent of the second connecting portion 130. For example, the first connecting portion 110 may comprise a tubular body slidably received inside a tubular body of the second connecting portion 130. The biasing element 160 (compressible or extensible) can be suitably positioned to cause the required biasing force. The first connecting portion 110 having a larger radial extent may be preferred, as the first connecting portion is to be manually used by the user to attach the delivery catheter, and the connector 100 is thus easier to use if the second connecting portion 130 is of a smaller diameter and received inside the first connecting portion 110 (i.e. lowers the likelihood of a user accidentally pushing the second connecting portion 130 in a distal direction, which would exert a direct force from the user to the loading tube 180).

Figure 2A:
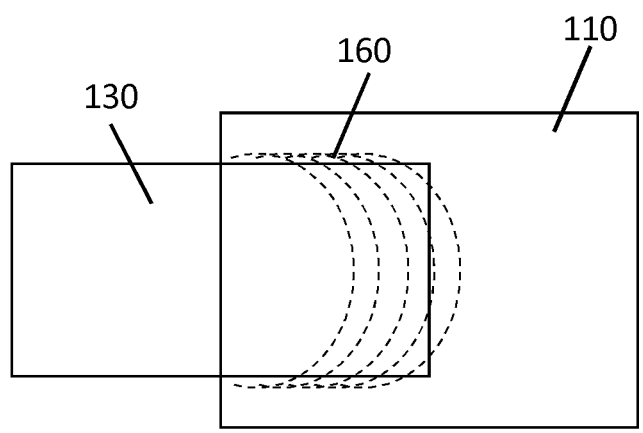
FIG. 2A shows a connector according to one or more embodiments in a first configuration.
Figure 2B:
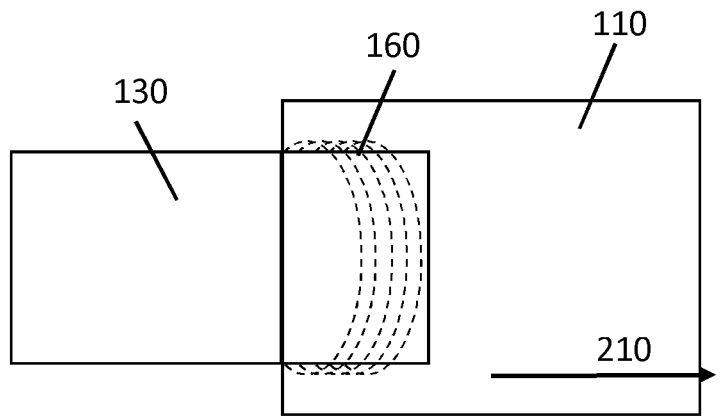
FIG. 2B shows the connector of FIG. 2A in a second configuration.
Figure 2C:
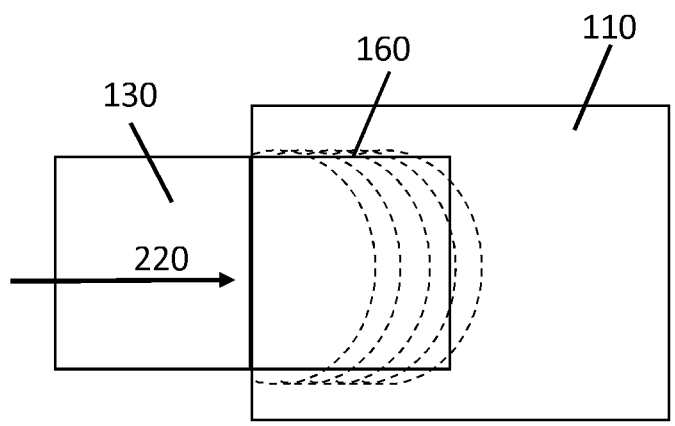
FIG. 2C shows the connector of FIG. 2A in a third configuration.

FIG. 2A schematically illustrates a connector 100 which uses a compression spring as the biasing element 160. A proximal portion of the spring is connected to the first connecting portion 110 and a distal portion of the spring is connected to the second connecting portion 130. In the illustrated example, the biasing element 160 is completely housed within the first connecting portion 110, which advantageously protects the biasing element from damage during use. In the example, when the first connecting portion 110 is moved in the distal direction (FIG. 2B, illustrated by arrow 210), the compression spring compresses and exerts a distal biasing force on the second connecting portion 130. The second connecting portion 130 then moves in a distal direction (FIG. 2C, illustrated by arrow 220) based on the biasing force exerted by the biasing element 160. It will be appreciated by the skilled person that other resiliently compressible biasing elements may be used in place of the compression spring.

Figure 3A:
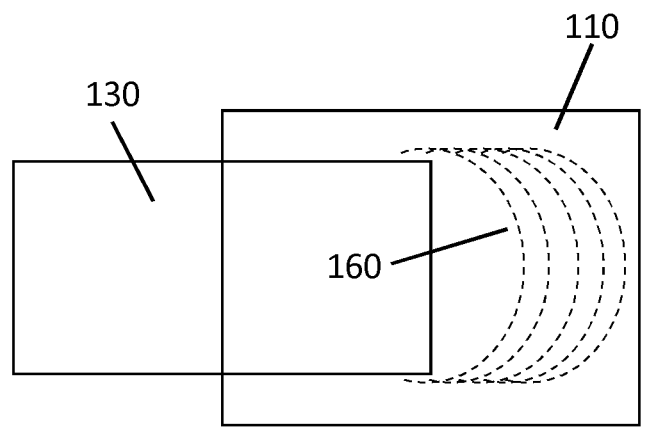
FIG. 3A shows a connector according to one or more embodiments in a first configuration.
Figure 3B:
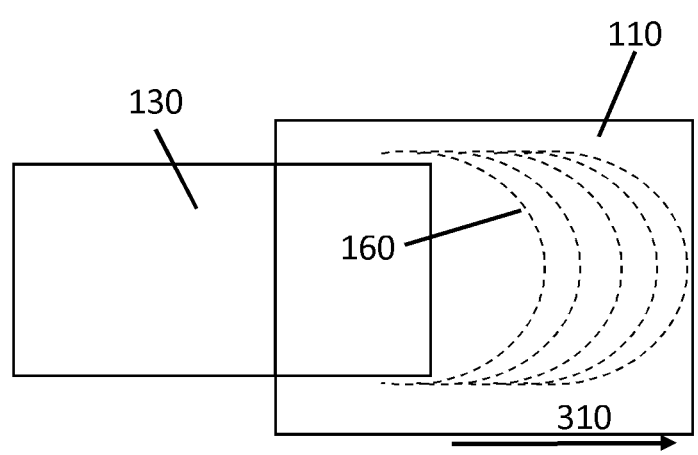
FIG. 3B shows the connector of FIG. 3A in a second configuration.
Figure 3C:
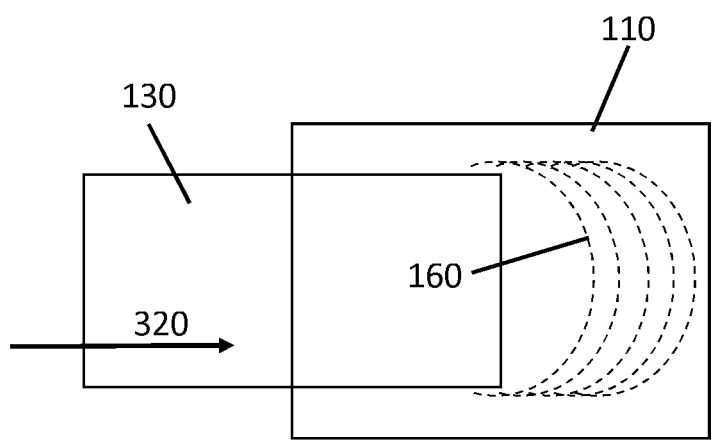
FIG. 3C shows the connector of FIG. 3A in a third configuration.

FIG. 3A illustrates a connector 100 which uses a tensile spring as the biasing element 160. A proximal portion of the spring is connected to the second connecting portion 13 and a distal portion of the spring is connected to the second connecting portion 130. In the illustrated example, the biasing element 160 is completely housed by the first connecting portion 110, again protecting the biasing element 160 from damage. Alternatively, the biasing element 160 may be situated partially or wholly externally to the first connecting portion 110. In the example, when the first connecting portion 110 is moved in the distal direction (FIG. 3B, illustrated by arrow 310), the compression spring stretches and exerts a distal biasing force on the second connecting portion 130. The second connecting portion 130 then moves in a distal direction (FIG. 3C, illustrated by arrow 320) based on the biasing force exerted by the biasing element 160. It will be appreciated by the skilled person that other resiliently extensible biasing elements may be used in place of the tensile spring.

Figure 4:
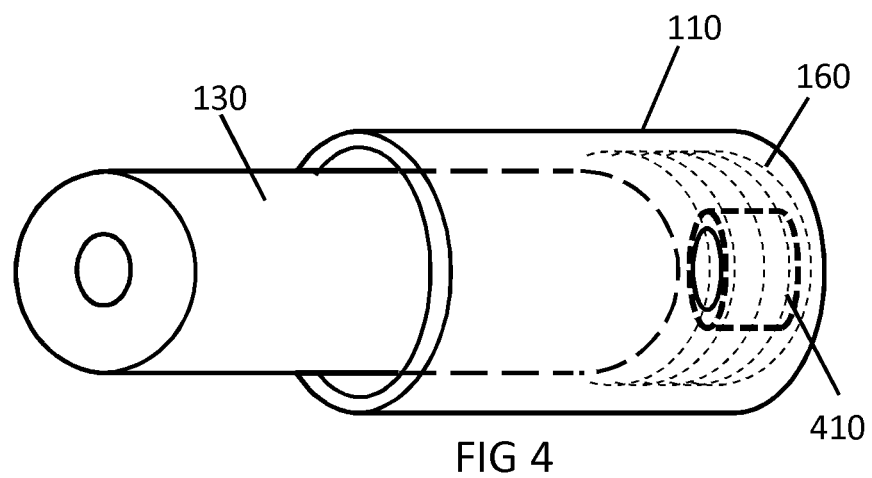
FIG. 4 shows a further connector according to one or more embodiments.

FIG. 4 illustrates another connector 100 according to the present disclosure. The connector 100 comprises a first connecting portion 110, a second connecting portion 130 and a biasing element 160 as in any of the previously disclosed examples. Additionally, the connector comprises an annular separating element 410 having a central lumen and configured to be positioned radially inward of, and extending longitudinally along the biasing element 160. Advantageously, the separating element 410 provides a central lumen for receiving the loading tube 180 and/or the delivery catheter 190, which is isolated from the biasing element 160. This prevents the medical implant from interacting with the biasing element 160 during transfer, thereby preventing damage to the medical implant during transfer from the loading tube to the delivery catheter, particularly when an intermediate longitudinal gap exists between the loading tube 180 and the delivery catheter 190.

Whilst the separating element 410 in the illustrated example is an individual element, another element of the connector 100 may act as the separating element 410. For example, in FIGS. 1A to 1C, 2 and 6 the second connecting portion 130 also acts as the separating element 410 by preventing interaction between the medical implant and the biasing element 160 during transfer.

Figure 5:
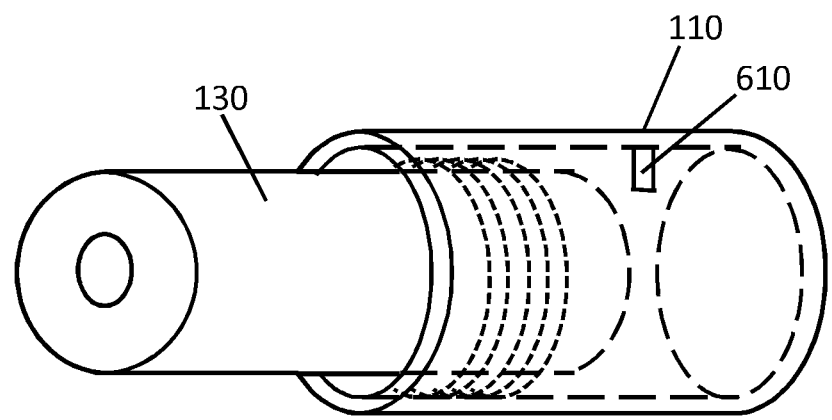
FIG. 5 shows a further connector according to one or more embodiments.

FIG. 5 illustrates a further connector 100 according to the present disclosure. The connector 100 comprises a first connecting portion 110, a second connecting portion 130 and a biasing element 160 as in any of the previously disclosed examples. The connector further comprises a stopping element (or stopper) 610. The stopping element 610 is configured to prevent the second connecting portion 130 from moving beyond a closest proximity to the proximal end 120 of the first connecting portion 110. Advantageously, this prevents the loading tube 180 from being pushed too far into the delivery catheter 190 (for example if the user accidentally pushes the second connecting portion 130 in the proximal direction during use). In the illustrated example, the stopping element 610 comprises a protrusion extending radially inward from the first connecting portion 110 which abuts a distal end of the second connecting portion 130 if the second connecting portion 130 is moved towards the distal end of the first connecting portion 110. In other examples, the stopping element 610 may comprise a protrusion extending radially outwardly from the second connecting portion 130 and configured to abut a portion of the first connecting portion 110. The first and second connecting portions may be selected to prevent movement of the second connecting portion 130 beyond a closest proximity to the distal end. For example, any suitable flange, protrusion, depression or combination could be used. Additionally, the relative shapes of the connecting portions could be designed to achieve this feature. For example, the stopper could be formed by a tapered shape of the first connecting portion 110.

It is noted that in some examples, an element of the connector could be configured to act as both a stopper 610 and a separating element 410 as described above. For example, the separating element 410 shown in FIG. 4 may have an outer diameter which is greater than the inner diameter of the second connecting portion 130, thereby preventing the second connecting portion 130 from moving beyond a closest proximity to the proximal end 120 of the first connecting portion 110.

Figure 6A:
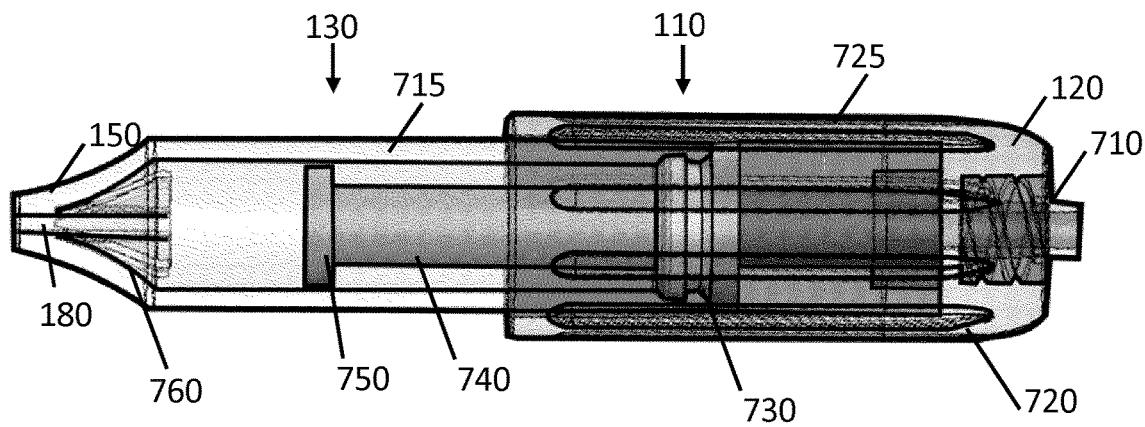
FIG. 6A shows a side view of a connector according to one or more embodiments.
Figure 6B:
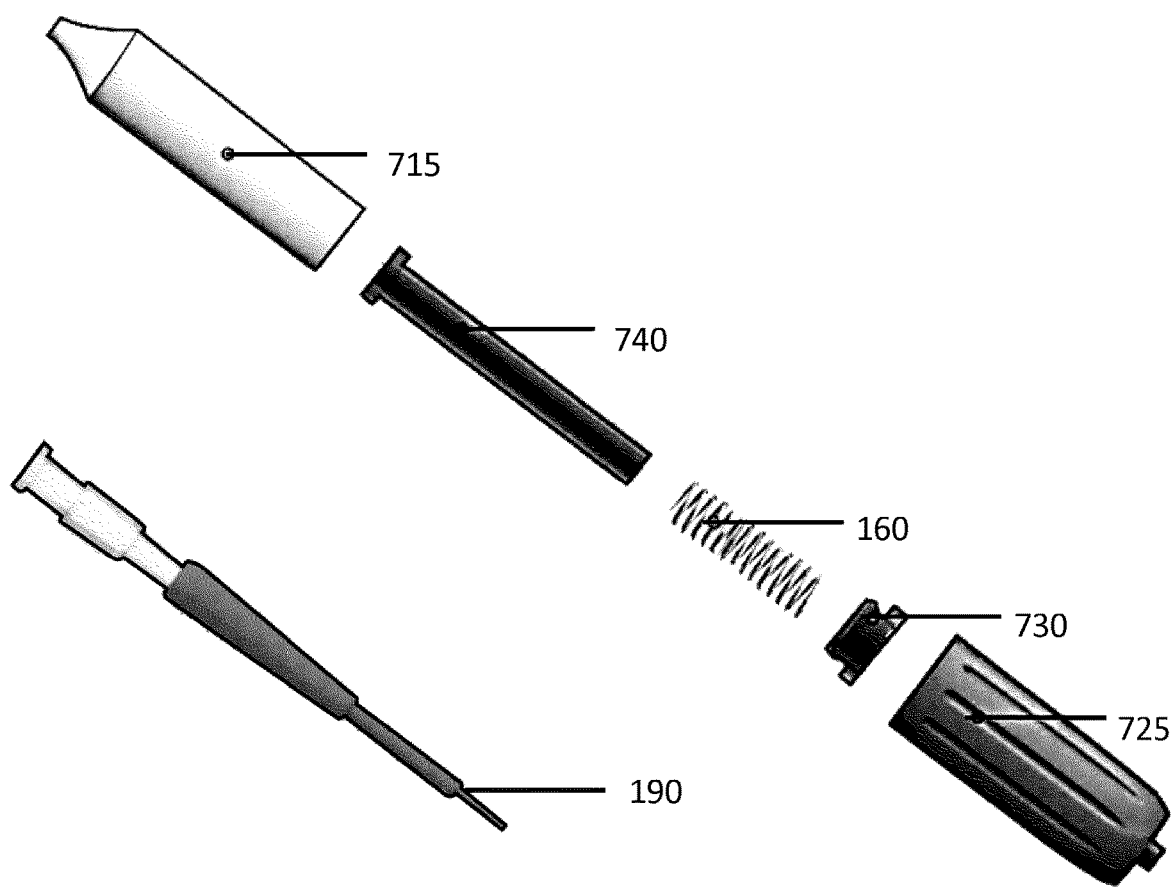
FIG. 6B shows an exploded view of the connector of FIG. 6A.

FIGS. 6A and 6B show yet another connector 100 according to the present disclosure. As in the case of the previously disclosed examples, the illustrated connector 100 comprises a first connecting portion 110 configured to receive a delivery catheter, a second connecting portion 130 configured to receive a delivery catheter and a biasing element (not shown in FIG. 6A) connecting the connecting portions. The first connecting portion 110 and the second connecting portion 130 comprise first and second tubular bodies 725, 715, with the second tubular body 715 being slidably received within the first tubular body 725. As in the previously disclosed examples, the biasing element 160 transmits a distal force exerted on the first connecting portion 110 to the second connecting portion 130. As discussed previously, for a given connector 100 with given dimensions and configurations when the delivery tube and delivery catheter are received, a biasing element 160 with a lower spring constant will exert a lower force on the loading tube 180. As such the biasing element 160 can be selected such that the force exerted on the loading tube does not exceed a threshold value. This prevents the loading tube from being forced too far into the catheter and being damaged (or radially collapsing), whilst also ensuring a proper connection between the loading tube 180 and delivery catheter 190

In the illustrated example, the second connecting portion 130 comprises a cap 730 disposed on a distal end of the second tubular body 715. The first connecting portion 110 additionally comprises an inner tubular body 740 extending into the second tubular body 715 (and slidably received) through the cap 730. The inner tubular body 740 additionally comprises a stopping portion (or stopping element) 750 inside the second tubular body 715. Separation of the first connecting portion 110 and the second connecting portion 130 is prevented by abutment of the cap 730 and the stopping portion 750.

The first connecting portion 110 may additionally comprise a grip 720 for assisting the user in connecting the delivery catheter 190. For example, the grip 720 may have a number of depressions in the surface of the first connecting portion 110.

Whilst any suitable mechanism may be used to connect the delivery catheter to the first connecting portion 110, in the illustrated example a Luer lock 710 is used. Likewise, any suitable mechanism for connecting the loading tube may be used, such as a frictional fit 760 having an inner diameter closely matched to the outer diameter of the loading tube it is configured to receive.

FIG. 6B shows an exploded view of the connector 100 shown in FIG. 6A. As can be seen from the exploded view, the individual components of the connector 100 can be easily assembled to form the connector 100. More particularly, in the illustrated example the biasing element 160 is a compression spring configured to be mounted on the inner tubular body 740 and configured to extend between the stopping portion 750 and the cap 730. The position of the compression spring between the cap and stopping portion provides a method of assembly as follows: the biasing element 160 and cap 730 are mounted on the inner tubular body 740. The inner tubular body 740 is then connected to the first tubular body 725, for example by an interference fit frictional fit, click fit or adhesive, at a distal portion of the first tubular body 725. The second tubular body 715 is then inserted into the first tubular body 725 until the cap is connected to the second tubular body 715 (for example via an interference, frictional or click fit or adhesive). It will be understood that in that case, the inner tubular body 740 also acts as a separating element 410.

Whilst the biasing element 160 is shown as a compression spring extending between the stopping portion 750 and the cap 730, other compressible biasing elements may be used. Additionally, other locations may be used for the biasing element 160 as discussed with respect to the previous examples. Alternatively, a tensile spring or other extensible biasing element may be used as discussed with respect to the previous examples.

It will also be appreciated by the skilled person that the grip 720 may be omitted.

Figure 7:
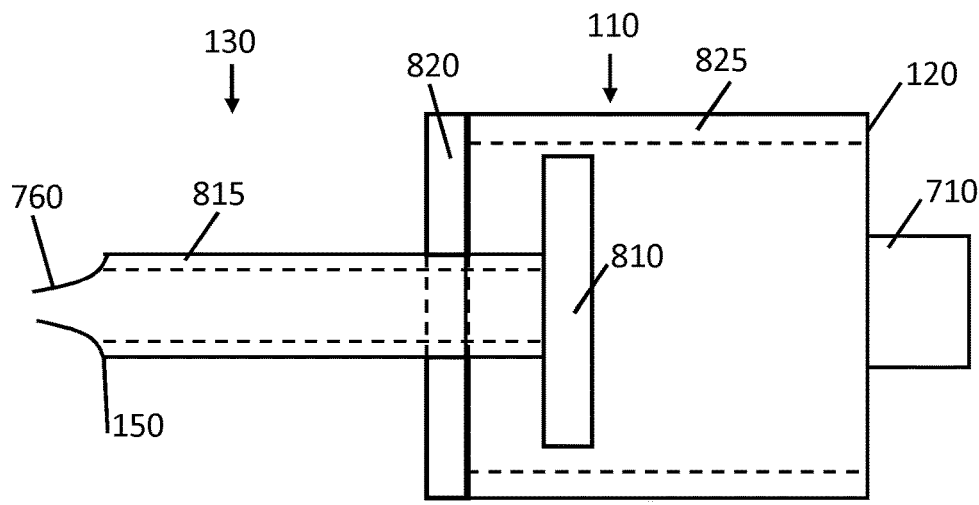
FIG. 7 shows another connector according to one or more embodiments.

FIG. 7 shows another connector 100 according to the present disclosure. As in the case of the previously disclosed examples, the illustrated connector 100 comprises a first connecting portion 110 configured to receive a delivery catheter, a second connecting portion 130 configured to receive a delivery catheter and a biasing element 160 connecting the connecting portions. The first and second connecting portions 110, 130 again comprise first and second tubular bodies 825, 815. The first connecting portion 110 comprises a cap 820 on a proximal end of the first tubular body 825. The second tubular body 815 extends into the first tubular body 825 (and is slidably received) through the cap 820. The second tubular body 815 comprises a stopping portion or stopping element 810 inside the first tubular body 825, such that separation of the first and second connecting portions is prevented by abutment of the cap 820 and the stopping portion 810.

As in previous examples, a compressible or an extensible biasing element 160 may be used. For example, the biasing element may comprise a compressible biasing element 160 such as a compression spring extending between the cap 820 and the stopping portion 810. In that configuration, the method of assembly may be as follows: the stopping portion 810 is connected to a distal end of the second tubular body 815 (or it may be unitary with the second tubular body). The biasing element 160 is then mounted on the second tubular body 815. The second tubular body 815 and the biasing element 160 is then inserted into the first tubular body 825. The cap 820 is mounted on and connected to the first tubular body 825 such that the second tubular body 815 extends through the cap 820. The cap 820 may be connected to the first tubular body 825 by any suitable mechanism, such as interference fit, frictional fit, click fit or via adhesive.

It will again be understood that whilst the biasing element 160 is shown as a compression spring extending between the stopping portion 810 and the cap 820, other compressible biasing elements may be used. Additionally, other locations may be used for the compressible biasing element 160 as discussed with respect to the previous examples. Alternatively, a tensile spring or other extensible biasing element may be used as discussed with respect to the previous examples.

It is noted that in the configuration where the biasing element 160 extends between the cap 820 and the stopping portion 810, the second tubular body acts as a separating element 410.

A connector according to the present disclosure may be formed by the following method:
  providing a first connecting portion having a first distal end configured to receive a delivery catheter;
  providing a second connecting portion having a second proximal end configured to receive a loading tube extending towards the distal end, the second connecting portion movably connected to the first connecting portion; and
  providing a biasing element connecting the first and second connecting portions, having a relaxed configuration in which the first distal end and the second proximal end are spaced apart by a predetermined distance, and configured to bias the first distal end and second proximal end to the relaxed configuration when the first distal end and second proximal end are moved apart from the relaxed configuration; such that when the loading tube is received, upon receiving the delivery catheter by the first connecting portion, the loading tube is biased to the delivery catheter to form a connection for the transfer of the implantable device.

It is noted that the order of steps noted above does not necessarily imply a chronological order. The loading tube 180 may also be connected to the second connecting portion 130 during manufacture to simplify the connecting process for a user.

As disclosed in some of the examples herein, the first connecting portion may comprise a first tubular body and an inner tubular body, the inner tubular body may comprises a stopping portion, and the seconding connecting portion may comprise a second tubular body and a cap, wherein the first tubular body is sized to receive the second tubular body and the second tubular body sized to receive the inner tubular body. In that case, the method may comprise (not necessarily chronologically):
  providing the biasing element;
  inserting the inner tubular body into a second distal end of the second tubular body; attaching the cap to a distal end of the second tubular body such that the inner tubular body extends through the cap and the stopping portion is housed by the second tubular body, and such that separation of the first connecting portion and the second connecting portion is prevented by abutment of the cap and the stopping portion; and
  attaching the inner tubular body to the first tubular body, wherein the second tubular body is slidable within the first tubular body.

The biasing element may comprise a resiliently compressible element or a resiliently extensible element and may be provided at any suitable location on the connector as discussed in the examples disclosed herein.

For example, the biasing element may comprise a resiliently compressible element (e.g. a compression spring) and be provided by connecting a proximal portion of the resiliently compressible element to the inner tubular body and a distal portion to the second tubular body. In some examples, the resiliently compressible element is provided to extend between the stopping portion and the cap.

Alternatively, the biasing element may comprise a resiliently extensible element (e.g. a tensile spring) and be provided by connecting a proximal portion of the resiliently extensible element to the second tubular body and a distal portion to the inner tubular body, or be provided by by connecting a proximal portion of the resiliently extensible element to the second tubular body and a distal portion to the second tubular body.

As disclosed in some examples herein, the first connecting portion may instead comprise a first tubular body and a cap, the second connecting portion comprising a second tubular body comprising a stopping portion, the first tubular body sized to receive the second tubular body, in which case the method may comprise (not necessarily chronologically):
  providing the biasing element;
  inserting the second tubular body into a proximal end of the first tubular body; and
  attaching the cap to a proximal end of the first tubular body, such that the second tubular body extends through the cap and the stopping portion is housed by the first tubular body, and such that separation of the first connecting portion and the second connecting portion is prevented by abutment of the cap and the stopping portion.

Again, the biasing element may comprise a resiliently compressible or extensible element.

For example, the biasing element may be a resiliently compressible element (e.g. compression spring) and may be provided by connecting a proximal portion of the resiliently compressible element to the first tubular body and a distal portion to the second tubular body. In some examples, the resiliently compressible element is provided to extend between the stopping portion and the cap.

Alternatively, the biasing element may be a resiliently extensible element (e.g. tensile spring) and be provided by connecting a proximal portion of the resiliently extensible element to the second tubular body and connecting a distal portion to the first tubular body.

The device may be provided to the user as a kit of parts comprising a connector according to any of the examples disclosed herein and a loading tube for being received by the connector. The loading tube may comprise a marker and the loading tube may be configured to be received by the second proximal end by inserting the loading tube into the second proximal end until the marker is positioned at the second proximal end. The user is readily able to assemble, from the visual cue of the marker, the connector and loading tube such that the loading tube will extend to the intended position in the connector when the delivery catheter is connected such that a secure connection for transfer of the medical implant is achieved.

Figure 8:
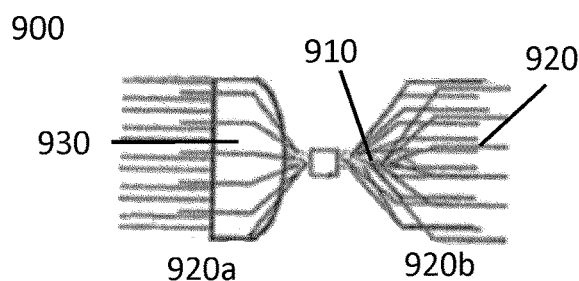
FIG. 8 shows an implant which can be transferred from a loading tube to a delivery catheter using a connector according to one or more embodiments.

The connectors described herein may be suitable for any medical implant, for example an embolisation device 900 as shown in FIG. 8 having a stem 910 and a plurality of flexible bristles 920 extending radially outwards from the stem. A first group of bristles may be grouped in a first bristle segment 920a configured to extend in a first longitudinal direction. A second group of bristles may be grouped in a second bristle segment 920b configured to extend in a second longitudinal direction opposite to the first longitudinal direction. The implant 900 may also comprise a flow restricting membrane 930, for example located longitudinally within one of the segments with bristles either side.

Figure 9A:
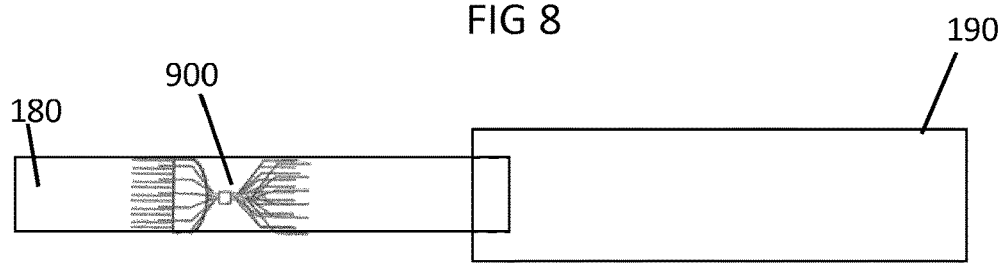
FIG. 9A shows an implant in a loading tube.
Figure 9B:
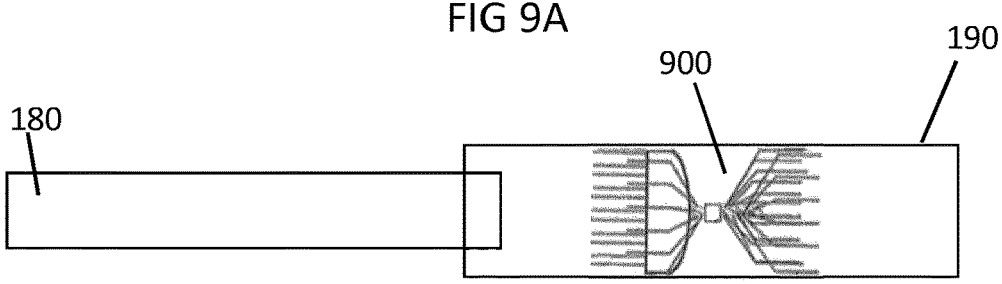
FIG. 9B shows an implant in a delivery catheter.
Figure 9C:
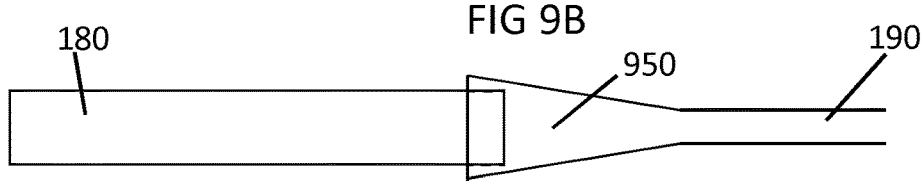
FIG. 9C shows a loading tube and a delivery catheter.

FIG. 9A shows an implant 900 in a loading tube 180. The loading tube 180 is connected to a delivery catheter 190 using any of the connectors disclosed herein (the connector is omitted from FIG. 9A for simplicity). Once the loading tube 180 is connected to the delivery catheter 190 using a connector, the implant 900 may be pushed distally through the loading tube 180 (for example using a pushing element extending longitudinally through the loading tube 180) and into the delivery catheter 190. FIG. 9B shows the implant 900 in the delivery catheter 190 after it has been transferred from the loading tube 180.

It will be appreciated that the features described with respect to one illustrated example are applicable to the other examples. For example, any suitable biasing element may be used in each example and may be positioned at any suitable point on the device as disclosed above.

Further, any of the disclosed connectors may additionally comprise one or more of a separating element, a stopping element, or any of the other elements described herein.

The various components of the connector may be made from any suitable material. For example, the components may be made of moulded plastic or metal.

All of the above are fully within the scope of the present disclosure, and are considered to form the basis for alternative embodiments in which one or more combinations of the above described features are applied, without limitation to the specific combination disclosed above.

In light of this, there will be many alternatives which implement the teaching of the present disclosure. It is expected that one skilled in the art will be able to modify and adapt the above disclosure to suit its own circumstances and requirements within the scope of the present disclosure, while retaining some or all technical effects of the same, either disclosed or derivable from the above, in light of the common general knowledge in this art. All such equivalents, modifications or adaptations fall within the scope of the present disclosure.

The invention claimed is:

1. A connector for transfer of an implantable device from a loading tube to a delivery catheter, comprising:
   a first connecting portion having a first distal end configured to hold a delivery catheter in a predetermined position;
   a second connecting portion having a second proximal end receiving a loading tube extending towards the first distal end, the second connecting portion movably connected to the first connecting portion; and
   a biasing element connecting the first and second connecting portions, having a relaxed configuration in which the first distal end and the second proximal end are spaced apart by a predetermined distance, and configured to bias the first distal end and second proximal end to the relaxed configuration when the first distal end and second proximal end are moved apart;
   such that when the delivery catheter is in the predetermined position, the loading tube is biased to the delivery catheter to form a connection having a continuous transition between the loading tube and the delivery catheter for the transfer of the implantable device.

2. The connector of claim 1, further comprising a separating element, wherein when the delivery catheter is received, the separating element is located radially between a proximal end of the delivery catheter and the biasing element; and/or
   wherein the biasing element is housed by at least one of the first connecting portion and the second connecting portion.

3. The connector of claim 1, wherein the biasing element comprises a resiliently extensible element having a proximal portion connected to the second connecting portion and a distal portion connected to the first connecting portion, preferably wherein the resiliently extensible element is a tensile spring; or
   wherein the biasing element comprises a resiliently compressible element having a proximal portion connected to the second connecting portion and a distal portion connected to the first connecting portion, preferably wherein the resiliently compressible element is a compression spring.

4. The connector of claim 1, further comprising a stopping element configured to prevent the first distal end and the second proximal end from moving closer than a closest distance to one another.

5. The connector of claim 1, wherein the first connecting portion comprises a first tubular body and the second connecting portion comprises a second tubular body slidable within the first tubular body, optionally wherein the first tubular body comprises an outer grip.

6. The connector of claim 1, wherein the second connecting portion comprises a second tubular body and a cap on a distal end of the second tubular body, and the first connecting portion comprises a first tubular body and an inner tubular body within the first tubular body, the inner tubular body extending into the second connecting portion through the cap, the inner tubular body comprising a stopping portion inside the second tubular body, such that separation of the first connecting portion and the second connecting portion is prevented by abutment of the cap and the stopping portion; or
   the first connecting portion comprises a first tubular body and a cap on a proximal end of the first tubular body, the first connecting portion extending into the second connecting portion through the cap, the second tubular body comprising a stopping portion inside the first tubular body, such that separation of the first connecting portion and the second connecting portion is prevented by abutment of the cap and the stopping portion.

7. The connector of claim 6, wherein the biasing element comprises a resiliently compressible element extending between the stopping portion and the cap, preferably wherein the resiliently compressible element is a compression spring.

8. A method of providing a connector for transfer of an implantable device from a loading tube to a delivery catheter, comprising:
   providing a first connecting portion having a first distal end configured to hold a delivery catheter in a predetermined position;
   providing a second connecting portion having a second proximal end;
   receiving a loading tube by the second connecting portion, the loading tube extending towards the first distal end, the second connecting portion movably connected to the first connecting portion; and providing a biasing element connecting the first and second connecting portions, having a relaxed configuration in which the first distal end and the second proximal end are spaced apart by a predetermined distance, and configured to bias the first distal end and second proximal end to the relaxed configuration when the first distal end and second proximal end are moved apart;

such that when the delivery catheter is in the predetermined position, the loading tube is biased to the delivery catheter to form a connection having a continuous transition between the loading tube and the delivery catheter for the transfer of the implantable device.

9. The method of claim 8, wherein the first connecting portion comprises a first tubular body and an inner tubular body, the inner tubular body comprising a stopping portion, and wherein the seconding connecting portion comprises a second tubular body and a cap, the first tubular body sized to receive the second tubular body and the second tubular body sized to receive the inner tubular body, the method comprising:

providing the biasing element;
inserting the inner tubular body into a second distal end of the second tubular body;
attaching the cap to a distal end of the second tubular body such that the inner tubular body extends through the cap and the stopping portion is housed by the second tubular body, and such that separation of the first connecting portion and the second connecting portion is prevented by abutment of the cap and the stopping portion; and
attaching the inner tubular body to the first tubular body, wherein the second tubular body is slidable within the first tubular body.

10. The method of claim 9, wherein the biasing element comprises a resiliently compressible element and is provided by connecting a proximal portion of the resiliently compressible element to the inner tubular body and a distal portion to the second tubular body, preferably wherein the resiliently compressible element is a compression spring.

11. The method of claim 9, wherein the biasing element comprises a resiliently extensible element and is provided by connecting a proximal portion of the resiliently extensible element to the second tubular body and a distal portion to the inner tubular body, preferably wherein the resilient extensible element is a tensile spring; or
wherein the biasing element comprises a resiliently extensible element and is provided by connecting a proximal portion of the resiliently extensible element to the second tubular body and a distal portion to the second tubular body, preferably wherein the resiliently extensible element is a tensile spring.

12. The method of claim 8, wherein the first connecting portion comprises a first tubular body and a cap, the second connecting portion comprises a second tubular body comprising a stopping portion, the first tubular body sized to receive the second tubular body, the method comprising:

providing the biasing element;
inserting the second tubular body into a proximal end of the first tubular body; and
attaching the cap to a proximal end of the first tubular body, such that the second tubular body extends through the cap and the stopping portion is housed by the first tubular body, and such that separation of the first connecting portion and the second connecting portion is prevented by abutment of the cap and the stopping portion.

13. The method of claim 12, wherein the biasing element is a resiliently compressible element and is provided by connecting a proximal portion of the resiliently compressible element to the first tubular body and a distal portion to the second tubular body, preferably wherein the resiliently compressible element is a compression spring.

14. The method of claim 12, wherein the biasing element is a resiliently extensible element and is provided by connecting a proximal portion of the resiliently extensible element to the second tubular body and connecting a distal portion to the first tubular body, preferably wherein the resiliently extensible element is a tensile spring.

15. The method of claim 10, wherein the resiliently compressible element is provided to extend between the stopping portion and the cap.

16. A kit of parts comprising a connector and a loading tube; the connector comprising:

a first connecting portion having a first distal end configured to hold a delivery catheter in a predetermined position;
a second connecting portion having a second proximal end configured to receive the loading tube extending towards the first distal end, the second connecting portion movably connected to the first connecting portion; and
a biasing element connecting the first and second connecting portions, having a relaxed configuration in which the first distal end and the second proximal end are spaced apart by a predetermined distance, and configured to bias the first distal end and second proximal end to the relaxed configuration when the first distal end and second proximal end are moved apart;
the loading tube comprising a marker and configured to be received by the second proximal end by inserting the loading tube into the second proximal end until the marker is positioned at the second proximal end;
such that when the loading tube is received with the marker positioned at the second proximal end and the delivery catheter is in the predetermined position, the loading tube is biased to the delivery catheter to form a connection having a continuous transition between the loading tube and the delivery catheter for the transfer of the implantable device.

* * * * *